(12) United States Patent
Craig et al.

(10) Patent No.: US 11,510,035 B2
(45) Date of Patent: Nov. 22, 2022

(54) WEARABLE DEVICE FOR MEASURING BODY KINETICS

(71) Applicants: Kyle Craig, Angola, IN (US); Hunter McMahan, Greenfield, IN (US); Bryce Hina, Warsaw, IN (US); Travis Riddle, Fort Wayne, IN (US); Robert Jay Kniskern, Fort Wayne, IN (US)

(72) Inventors: Kyle Craig, Angola, IN (US); Hunter McMahan, Greenfield, IN (US); Bryce Hina, Warsaw, IN (US); Travis Riddle, Fort Wayne, IN (US); Robert Jay Kniskern, Fort Wayne, IN (US)

(*) Notice: Subject to any disclaimer, the term of this patent is extended or adjusted under 35 U.S.C. 154(b) by 588 days.

(21) Appl. No.: 16/671,566

(22) Filed: Nov. 1, 2019

(65) Prior Publication Data
US 2020/0145797 A1 May 7, 2020

Related U.S. Application Data

(60) Provisional application No. 62/757,118, filed on Nov. 7, 2018.

(51) Int. Cl.
*H04W 4/38* (2018.01)
*A61B 5/11* (2006.01)
(Continued)

(52) U.S. Cl.
CPC ............ *H04W 4/38* (2018.02); *A41H 1/02* (2013.01); *A61B 5/11* (2013.01); *A63B 24/0006* (2013.01); *G06F 1/163* (2013.01)

(58) Field of Classification Search
CPC ......... H04W 4/38; H04W 4/80; H04W 4/027; A41H 1/02; A61B 5/11; A61B 2560/0223;
(Continued)

(56) References Cited

U.S. PATENT DOCUMENTS 8,165,844 B2* 4/2012 Luinge ................ A61B 5/1126
382/128
8,444,564 B2 5/2013 Mahfouz et al.
(Continued)

FOREIGN PATENT DOCUMENTS

WO WO 2016/044251 A1 3/2016
WO 2016/053459 A1 4/2016
(Continued)

OTHER PUBLICATIONS

IOP Science, IP Address: 208.78.168.65, Wearable Sensors, Applications, Design & Implementation, Authors: T. Islam & S.C. Mukhopadhayay IOP Publishing Ltd 2017.

*Primary Examiner* — Christopher M Brandt (57) ABSTRACT

A System for Measuring Body Kinetics includes a wearable device configured to be wrapped around a joint. A microprocessor is attached to the wearable device. One or more Inertial Measurement Units (IMUs) are connected to the microprocessor and arranged on the wearable device. The IMUs are arranged and configured to provide kinetic data concerning the joint to the microprocessor. A wireless transmission component is connected to the microprocessor. The microprocessor is configured to receive kinetic data from the IMUs, and to transmit the kinetic data by way of the wireless transmission component to a central processor or other device. An algorithm resides within the microprocessor or the central processor or other device, and is configured to determine the position of each IMU from the kinetic data. The wearable device may be constructed of fabric, strap, adhesive tape, or a combination thereof.

21 Claims, 5 Drawing Sheets

(51) Int. Cl.
*G06F 1/16* (2006.01)
*A41H 1/02* (2006.01)
*A63B 24/00* (2006.01)

(58) Field of Classification Search
CPC ... A61B 5/0002; A61B 5/0059; A61B 5/1114; A61B 5/1121; A61B 5/4585; A61B 5/4595; A61B 5/6828; A61B 5/6829; A61B 5/7246; A61B 2562/0219; A63B 24/0006; G06F 1/163; A41D 13/1281

See application file for complete search history.

(56) References Cited

U.S. PATENT DOCUMENTS

| | | |
|---|---|---|
| 9,439,599 B2 | 9/2016 | Thompson et al. |
| 9,717,958 B1 | 8/2017 | Tran et al. |
| 9,737,239 B2 | 8/2017 | Kimmel |
| 9,750,977 B2 | 9/2017 | Yuen et al. |
| 9,752,861 B2 | 9/2017 | Tata et al. |
| 9,757,640 B2 | 9/2017 | Weast et al. |
| 9,759,738 B2 | 9/2017 | Oleson et al. |
| 9,767,709 B2 | 9/2017 | Ellis |
| 10,123,751 B2 | 11/2018 | Petterson et al. |
| 2010/0204616 A1 | 8/2010 | Shears et al. |
| 2015/0257682 A1* | 9/2015 | Hansen ............... A61B 5/7475 382/103 |
| 2016/0220808 A1 | 8/2016 | Hyde et al. |
| 2016/0256082 A1 | 9/2016 | Ely et al. |
| 2016/0324442 A1 | 11/2016 | Zdeblick |
| 2016/0338621 A1 | 11/2016 | Kanchan et al. |
| 2017/0103541 A1 | 4/2017 | Bellusci et al. |
| 2017/0238849 A1 | 8/2017 | Chapman et al. |
| 2018/0070864 A1 | 3/2018 | Schuster |
| 2018/0160966 A1 | 6/2018 | Inan et al. |
| 2018/0184735 A1 | 7/2018 | Longinotti-Buitoni et al. |

FOREIGN PATENT DOCUMENTS

| | | |
|---|---|---|
| WO | WO 2017/088068 A1 | 6/2017 |
| WO | WO 2018/140429 A1 | 8/2018 |

* cited by examiner

WEARABLE DEVICE FOR MEASURING BODY KINETICS

CROSS-REFERENCE TO RELATED APPLICATIONS

The present application claims priority to U.S. Provisional No. 62/757,118, filed Nov. 7, 2018, the entire contents of all of which are herein incorporated by reference.

BACKGROUND

Field of Invention

Embodiments described herein generally relate to a Wearable Device for Measuring Body Kinetics. The Wearable Device for Measuring Body Kinetics measures and analyzes body kinetics, in order to help therapists and other medical personnel work with recovering patients, and to help trainers work with athletes.

Related Art

It is known to measure human body kinetics, or the location of points on the human body as the body moves. This may be done for the purpose of diagnosing injuries, measuring disease progression, or for therapeutic reasons. Alternately, it may be done in order to help athletes, particularly peak athletes, maximize their performance through controlled motion during training. Most wearable sensors used for this purpose rely on visual approximations, so that the location of each point to be measured on the body is determined based on its line-of-sight relationship with an observer or recording device. As a result, measurement is often limited, inaccurate, and impractical for use in many situations.

Accordingly, there is an unmet need for a Wearable Device for Measuring Body Kinetics that is versatile, yet more accurately measures the location of points on the body.

SUMMARY

Embodiments described herein relate to a Wearable Device for Measuring Body Kinetics. The Wearable Device for Measuring Body Kinetics includes one or more wearable devices and a Software as a Service (SAAS) network that cooperates to measure and analyze body kinetics. The Wearable Device for Measuring Body Kinetics may be used, for non-limiting example, by therapists in working with patients, or by trainers in working with athletes, as mentioned previously. The Wearable Device for Measuring Body Kinetics may further be used in related fields, such as veterinary applications. The several embodiments herein use wearable devices worn around the knees and ankles, but this is not to be construed as limiting the scope of the Wearable Device for Measuring Body Kinetics in any way, which may include embodiments that may be worn, for non-limiting example, around the neck, shoulders, back, elbows, wrists, hips, knees, ankles, or any combination thereof.

Product Description

The Wearable Device for Measuring Body Kinetics has multiple Inertial Measurement Units (IMUs) connected to a microprocessor that has both processing and wireless transmission capabilities. The multiple IMUs are positioned on the wearable device in such a way as to provide information regarding the position and motion of the joint. The IMUs function as radio frequency identified (RFID) position sensors by way of at least one, and possibly multiple accelerometers, which may provide linear position, linear velocity, linear acceleration, and/or rate of change of linear acceleration in three axes. The IMUs may further function as gyroscopic sensors, providing angular position, angular velocity, angular acceleration, and/or rate of change of angular acceleration data about three axes. The position and/or motion sensing and/or gyroscopic IMUs may be embodied as thin film sensors. The IMUs may further be provided with one or more infrared transceiver/receiver, which may be used alone or with another optical sensor to detect movement and/or heat representing blood flow or metabolic activity at or under the skin surface. In this capacity, the IMUs may also be embodied as thin film sensors.

The infrared transceiver/receivers and/or optical sensors, which are attached to the Wearable Device for Measuring Body Kinetics and oriented toward the patient's body, pick up this movement and/or thermal data by way of wavelengths of light emitted or reflected in the infrared and/or near infrared spectrum, and then transmit it through one or more circuits to the microprocessor. Infrared and/or near infrared spectrum may include light having a wavelength of about 0.75 μm to about 1.4 μm, or being in the frequency range of about 214 THz to about 400 THz. The wavelength of light received by the infrared transceiver/receivers and/or optical sensors may be fixed, or may be allowed to fluctuate or be actively varied, so that the movement and/or thermal data remains distinct from, for non-limiting example, background or general body heat. The use of near infrared light allows the transceiver/receivers and/or optical sensors to function without causing harm to the user. Alternately, the IMUs may be separate from the infrared transceiver/receivers, so that the IMUs function as RFID position and/or motion sensors, accelerometers, and/or gyroscopic sensors, and the infrared transceiver/receivers and/or optical sensors function as movement and/or thermal sensors. Whether the IMUs and infrared transceiver/receivers are integrated or separate, the information sensed by the IMUs and infrared transceiver/receivers is packed up and transmitted wirelessly to a central processor or another device, such as, for non-limiting example, a smart phone, tablet, computer, or other device, where the data can be processed.

The processed data can be used to yield the following:

Kinetic data, such as linear position, linear velocity, linear acceleration, and/or linear rate of change of acceleration, angular position, angular velocity, angular acceleration, and/or rate of change of angular acceleration, whether such data is produced directly from the IMUs or derived therefrom;

Impact force and/or shock;

A spring model of the body and/or the joints thereof;

Information regarding superficial muscles, tendons, and ligament fibers during movement;

Information regarding blood flow, oxygenation, and/or metabolic activity;

Pairing and/or correlation of the qualitative infrared sensor derived information with real-time quantitative kinetic data; and A 3-dimensional "mesh" model of the wearable device, and thereby of the body and/or joints thereof beneath.

Device Description

The Wearable Device for Measuring Body Kinetics consists of a wearable fabric, strap, and/or tape device with an attached electronic circuit. In a fabric embodiment, the fabric is cut to a shape based on the joint or body area that it will cover. The wearable device may be applied to the body by wrapping the wearable device around a joint, for non-limiting example an ankle, knee, hip, and etcetera. The wrap may be secured via a hook and loop fastener, with the top of the fabric having the loop component of the hook and loop fastener, and the underside of the fabric having the hook component of the hook and loop fastener, or vice versa. The fabric of the wearable device may be made to stretch, preferably to at least 150% of its relaxed dimensions, while retaining its original shape even through numerous uses. The stretchy characteristic of the fabric of the wearable device allows a tight fit to the joint for greater accuracy of the data, while accommodating varying body sizes. The wearable device may be made from a fabric that is machine washable and dryable, and may further be made from a fabric that "wicks away" moisture from the patient's skin to minimize the accumulation of sweat and moisture. The fabric of the wearable device may be further chosen to be strong and durable, to exhibit good wear characteristics, to tolerate overstretching, and to be comfortable to the user.

In a strap embodiment, the wearable device may be embodied as a pattern of fabric or webbing straps sewn together to position the circuit and its IMUs in their correct locations, similar to the fabric embodiment(s). The strap embodiment(s) accomplish this while avoiding contact in other areas, such as a wound site, as a non-limiting example. Additionally, certain embodiments of the wearable device may combine aspects of the fabric embodiment(s) and the strap embodiment(s), so that the wearable device is partially of fabric construction, and is partially of strap construction. The wearable device may also be embodied as a pattern or construct of adhesive tape or other adhesive arrangement, such as an adhesive patch, as a non-limiting example. In this embodiment(s), the adhesive tape or other adhesive arrangement with the circuit and its IMUs attached positively locates the IMUs relative to the joint, thereby further providing greater accuracy of the data. Certain embodiments of the wearable device may again combine aspects of the fabric embodiment(s), the strap embodiment(s), and or the adhesive tape or other adhesive arrangement embodiment(s), so that the wearable device is partially of fabric construction, is partially of strap construction, and/or is partially of adhesive tape or other adhesive arrangement construction.

The circuit includes the multiple IMUs, preferably at least three IMUs, even more preferably at least eight IMUs, with the quantity of IMUs to be used depending on the desired quantity or resolution of data. One or more of the IMUs may be integrated into a pivoting or articulating joint component, if the wearable device is so provided. The circuit may include the multiple infrared transceiver/receivers and/or optical sensors, where the multiple infrared transceiver/receivers and/or optical sensors are not integrated with the multiple IMUs. The circuit may, and in at least one embodiment does, further include a flexible power source and a Data Acquisition Component (DAQ)/flexible processing board/micro-processing unit. The circuit may, and in at least one embodiment does, further include a wireless transmission component, which may include a device capable of processing and wireless transmission of data, for non-limiting example a Bluetooth® chip. The circuit may, and in at least one embodiment does, also include a printed receiver coil for wireless charging with AC/DC conversion. Each of the circuit, the IMUs, the infrared transceiver/receivers and/or optical sensors, the flexible power source, the DAQ/flexible processing board/micro-processing unit, the wireless transmission component, and the printed receiver coil, and other miscellaneous components may be fully waterproof.

The components of the circuit may be laid out in a specific configuration for each body joint. The circuit may be printed on a thin flexible film to allow comfortable movement while protecting the circuit. The leads to the IMUs and/or infrared transceiver/receivers may be printed in such a way that allows them to stretch with the fabric, for non-limiting example by arranging the leads to each describe a sinusoidal line so that the wires straighten without breaking when the fabric stretches. The circuit may be attached to the fabric via hook and loop fastener, in which case the areas where the circuit is to be attached are mapped out on the fabric either through markings and/or by only placing the hook or loop part where it's needed.

In an alternate embodiment, the multiple IMUs and/or the multiple infrared transceiver/receivers and/or optical sensors, whether integrated or not, may operate independently from the primary circuit. In this embodiment, each of the multiple IMUs and/or the multiple infrared transceiver/receivers and/or optical sensors may be independently powered, and may communicate with the DAQ/flexible processing board/micro-processing unit and/or the wireless transmission component by way of a local wireless network. The local wireless network may operate using, for non-limiting example, RFID chips, Wi-Fi, Bluetooth, radio frequency transceivers/receivers, and/or two-way radio frequency communication. Communication by way of the local wireless network may allow for two-way communication between the DAQ/flexible processing board/micro-processing unit and/or the wireless transmission component, and the multiple IMUs and/or the multiple infrared transceiver/receivers and/or optical sensors, using for non-limiting example I2C, SPI, or other type of master-slave communication.

As with previous embodiments, any circuit boards required by the multiple IMUs and/or the multiple infrared transceiver/receivers and/or optical sensors and/or additional supporting electrical components may not be completely rigid. Rather, such circuit boards may be at least semi-flexible. The power sources for each sensor may consist of, for non-limiting example, thin and flexible batteries, current generated from the RFID chips, and/or dime batteries. This arrangement allows additional flexibility in placement of the multiple IMUs and/or the multiple infrared transceiver/receivers and/or optical sensors on the wearable device.

Hardware Description

Each IMU may be, and in at least one embodiment is, a combined accelerometer and gyroscope with six degrees of freedom. The IMUs may each give readings on linear position, linear velocity, linear acceleration, and/or rate of change of linear acceleration, and angular position, angular velocity, angular acceleration, and/or rate of change of angular acceleration, and/or any combination thereof, as noted previously. The frequency of readings may vary from about 10 Hz minimum to about 200 Hz, for non-limiting example. Each of the IMUs may be provided with connections compatible with digital pins having Inter-Integrated Circuit (I2C) and/or Serial Peripheral Interface (SPI) wiring capabilities. One or more of the IMUs on each wearable device may be, and in at least one embodiment is, specialized, for non-limiting example having a high sensitivity to vibration, or optimized for use in determining force due to impact. The one or more specialized IMUs may, and in at least one embodiment does, also have infrared transceiver/receivers and/or optical sensors in the same way that the non-specialized IMUs may have infrared transceiver/receivers and/or optical sensors. In this way, the specialized IMUs, if used, provide data on vibration, force, and impact, which is provided to the microprocessor, along with the linear position, linear velocity, linear acceleration, and/or rate of change of linear acceleration, and angular position, angular velocity, angular acceleration, and/or rate of change of angular acceleration provided by the non-specialized IMUs.

The DAQ/flexible processing board/micro-processing unit may be, and in at least one embodiment is, able to take in and store data from the multiple specialized and/or non-specialized IMUs and/or from the multiple infrared transceiver/receivers and/or optical sensors. This may occur, for non-limiting example, during a given test session. Thereafter, the DAQ/flexible processing board/micro-processing unit may, and in at least one embodiment does, pack up and transmit the data wirelessly to the smart phone, tablet, computer, or other device. The data may be stored in digital format until it can be transferred to the smart phone, tablet, computer, or other device. Alternately, the DAQ/flexible processing board/micro-processing unit may pack up and transmit the data continuously to the smart phone, tablet, computer, or other device during a given test session.

The DAQ/flexible processing board/micro-processing unit may have processing and/or wireless transmission capabilities, and in at least one embodiment has both. Non-limiting examples of the wireless transmission capabilities include wireless personal area network (WPAN), Wi-Fi, Bluetooth®, Radio Frequency (RF), Infrared Data Association (IrDA), Wireless USB, Zigbee, and etcetera. The DAQ/flexible processing board/micro-processing unit may, and in at least one embodiment does, have a 16-bit operation and in any case has sufficient memory to store its programming. The DAQ/flexible processing board/micro-processing unit may, and in at least one embodiment does, have the capacity to be provided with an electronic serial number to be read by software running on the smart phone, tablet, computer, or other device. The software may use the serial number to determine, for non-limiting example, the device's compliance, data resolution, joint type, and/or unit number.

The flexible power source may supply DC current at five volts, for non-limiting example, to the circuit when the wearable device is in use, and may not provide any current to the circuit when the wearable device is not in use. The flexible power supply may step the voltage up from three volts as provided by the battery to the five volts needed, for non-limiting example, by the DAQ/flexible processing board/micro-processing unit. The flexible power source provides enough power to the circuit to operate the DAQ/flexible processing board/micro-processing unit, the wireless transmission component, and the IMUs for a given test session, preferably for at least one hour, even more preferably for longer than one hour. The flexible power source and/or DAQ/flexible processing board/micro-processing unit may be provided with an indicator that communicates the remaining power level and/or indicates when the power level remaining in the flexible power source is low and needs to be recharged. The flexible power source may be, and in at least one embodiment is, physically flexible, in order to bend with the deformations of the wearable device during use. The flexible power source may be covered or encased to protect the skin of the user from any battery leakage.

The flexible power source may be, and in at least one embodiment is, rechargeable. In order to facilitate charging of the flexible power source, the flexible power source may be, and in at least one embodiment is, provided with a wireless charging receiver coil capable of receiving a charge of, for non-limiting example, one amp per hour of AC current. The wireless charging receiver coil may be printed in a flexible configuration, in order to deform with the wearable device, or may be small enough and positioned on the wearable device in a location that will not experience significant movement or stretching under ordinary use. In either case, the wireless charging receiver coil is configured to lay flat during charging, in order to be in a charging coil's magnetic field. The wireless charging receiver coil and/or the flexible power source may be provided with an AC to DC converter in order to provide DC current to the batteries of the flexible power source.

Use of Data

As noted previously, the data sensed by the IMUs and/or the infrared transceiver/receivers may be wirelessly transmitted to a central processor or mobile device, such as for non-limiting example a phone or tablet, computer, or other device, for processing. The data may also be sent to a cloud system for computation and/or storage. To calibrate the wearable device, the wearable device may be laid flat to establish a beginning position. An algorithm within the DAQ/flexible processing board/micro-processing unit and/or within the central processor or other device then uses the data to determine the position of each point. This establishes the coordinates of the IMUs in a flat plane configuration as a starting position.

As the user wraps the wearable device around his or her joint, the positions of the IMUs, which may appear on a computer screen, may change based on the motion data received from the wearable device. These so-called points or "nodes" correspond to the real-time location of the IMUs. Each IMU may, therefore, have its own coordinate that may be presented in a 3-D Scatter Plot to provide a visual for motion. Laying the wearable device flat, and subsequently wrapping the wearable device around the joint for the purpose of calibration makes it easier for the algorithm to establish starting positions of the IMUs in the system, and may further allow for determining certain metrics. For non-limiting example, certain measurements of diameter and circumference of areas of the body above and below the joint that would normally have to be done manually may be accomplished by this method.

The nodes in the computer screen display may be connected by lines to form a wireframe visual of the wearable device. The coordinates of each node may change based on the movement data from the IMUs. Curvature in the lines may be calculated both during calibration to reflect the radial properties of the body, and may be refined during testing when there is angular movement. The IMUs and their onscreen nodes may be located at critical points for gathering data on each joint. As a non-limiting example, in an embodiment of the wearable device for use on the foot, the IMUs and their onscreen nodes may be placed around the ankle, along the inside of the arch of the foot, and at the toes.

According to one embodiment of the invention, a System for Measuring Body Kinetics includes a wearable device configured to be wrapped around a joint. A microprocessor is attached to the wearable device. One or more IMUs are connected to the microprocessor and arranged on the wearable device. The IMUs are arranged and configured to provide kinetic data concerning the joint to the microprocessor. One or more infrared transceiver/receivers are also connected to the microprocessor and arranged on the wearable device. The infrared transceiver/receivers are arranged and configured to provide qualitative movement data by way of sensing wavelengths of light emitted or reflected in the near infrared spectrum. A wireless transmission component is connected to the microprocessor. The microprocessor is configured to receive kinetic data from the IMUs and qualitative movement data from the infrared transceiver/receivers, and to transmit the kinetic data and the qualitative movement data by way of the wireless transmission component to a central processor or other device. An algorithm resides within the microprocessor or the central processor or other device. The algorithm is configured to determine the position of each IMU from the kinetic data, and to pair or correlate the qualitative movement data with the kinetic data.

According to another embodiment of the invention, a Wearable Device for Measuring Body Kinetics, includes a wearable device configured to be wrapped around a joint. A microprocessor is attached to the wearable device. One or more IMUs are connected to the microprocessor and arranged on the wearable device. The IMUs are arranged and configured to provide kinetic data concerning the joint to the microprocessor. One or more Infrared transceiver/receivers are also connected to the microprocessor and arranged on the wearable device. The infrared transceiver/receivers are arranged and configured to provide qualitative movement data by way of sensing wavelengths of light emitted or reflected in the near infrared spectrum. A wireless transmission component is connected to the microprocessor. The microprocessor is configured to receive kinetic data from the IMUs and qualitative movement data from the infrared transceiver/receivers, and to transmit the kinetic data and the qualitative movement data by way of the wireless transmission component to a central processor or other device. An algorithm resides within the microprocessor and is configured to pair or correlate the qualitative movement data with the kinetic data.

According to another embodiment of the invention, a Method for Measuring Body Kinetics includes several steps. The first step is configuring a wearable device to be wrapped around a joint. The second step is attaching a microprocessor to the wearable device. The third step is arranging one or more IMUs on the wearable device and connecting the IMUs to the microprocessor. The fourth step is configuring the IMUs to provide kinetic data concerning the joint to the microprocessor. The fifth step is arranging one or more infrared transceiver/receivers on the wearable device and connecting the one or more infrared transceiver/receivers to the microprocessor. The sixth step is configuring the infrared transceiver/receivers to provide to the microprocessor qualitative movement data sensed by way of wavelengths of light emitted or reflected in the near infrared spectrum. The seventh step is configuring the microprocessor to receive the kinetic data from the IMUs and to receive the qualitative movement data from the infrared transceiver/receivers. The eighth step is connecting a wireless transmission component to the microprocessor. The ninth step is transmitting the kinetic data and the qualitative movement data by way of the wireless transmission component to a central processor or other device. The tenth step is configuring an algorithm residing within the microprocessor, the central processor, or other device to determine the position of each IMU from the kinetic data, and to pair or correlate the qualitative movement data with the kinetic data.

Embodiments of the Wearable Device for Measuring Body Kinetics are able to improve research in human movement and dynamics, as well as improve performance analysis of athletes. For non-limiting example, embodiments of the Wearable Device for Measuring Body Kinetics may allow tracking of motion over long distances, in order to measure gait for long distance runners. Embodiments of the Wearable Device for Measuring Body Kinetics are further able to contribute to the diagnosis of a damaged joint or biomechanical misalignment, as well as to the monitoring of a patient after an operation to repair a joint or after a total joint replacement. The software system of the Wearable Device for Measuring Body Kinetics may also assist healthcare providers in coordinating care associated with a body joint. For non-limiting example, the Wearable Device for Measuring Body Kinetics may be used to provide gait analysis in physical therapy, or diagnosis of weak muscles, tendons, and ligaments.

The multiple infrared transceiver/receivers and/or optical sensors, if provided, may match tendon, ligament, and/or muscle movement with quantitative data provided by the Wearable Device for Measuring Body Kinetics. Embodiments of the Wearable Device for Measuring Body Kinetics may allow a user to track the dispersion of impact energy during walking, jumping, running, and etcetera. Other embodiments of the Wearable Device for Measuring Body Kinetics incorporating sensors on the foot and ankle may provide a realistic view of arch descent, in order to test dynamic forces in shoes, barefoot, landing, pronation, supination, and more. Embodiments of the Wearable Device for Measuring Body Kinetics may be mass marketed for personal use, or may be marketed directly to the athletic and healthcare industries.

DESCRIPTION OF THE DRAWINGS

The above-mentioned and other features of embodiments of Wearable Device for Measuring Body Kinetics, and the manner of their working, will become more apparent and will be better understood by reference to the following description of embodiments of the Wearable Device for Measuring Body Kinetics taken in conjunction with the accompanying drawings, wherein.

Corresponding reference numbers indicate corresponding parts throughout the several views. The exemplifications set out herein illustrate embodiments of the Wearable Device for Measuring Body Kinetics, and such exemplifications are not to be construed as limiting the scope of the claims in any manner.

DETAILED DESCRIPTION

Figure 1:
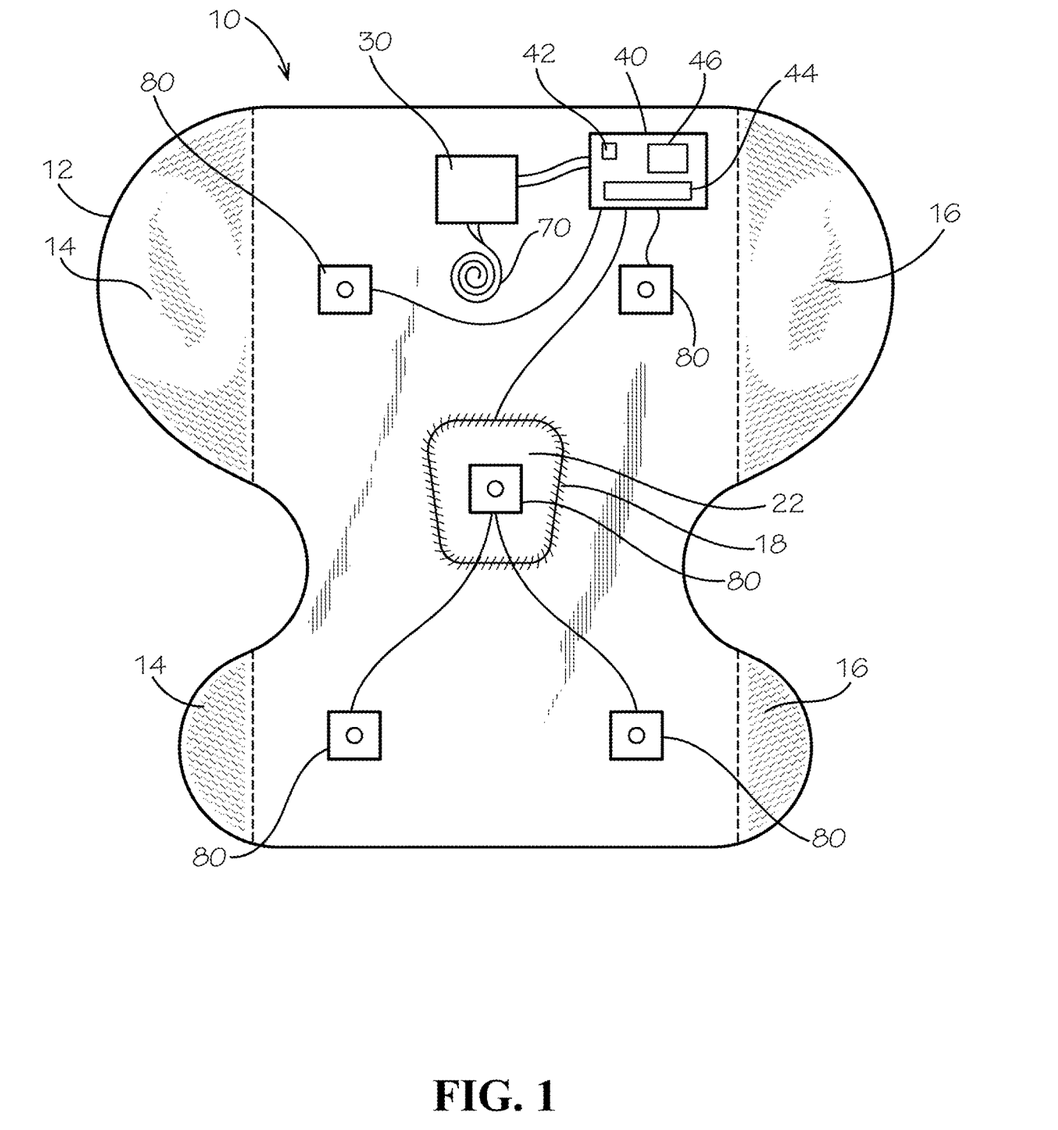
FIG. 1 is a plan view of an embodiment of a Wearable Device for Measuring Body Kinetics, as described herein.

Referring now to FIG. 1, a plan view is shown of an embodiment of a wearable device 10 arranged to be placed around a patient's knee. The wearable device 10 is constructed of fabric, and is provided with a hook and loop closure 12, wherein the hooks 14 are located on the outer surface at one end of the wearable device 10 and the loops 16 are on located on the inner surface at the other end of the wearable device 10. A flexible processing board/micro-processing unit/DAQ 40 is connected to at least one IMU 80, preferably at least three IMUs 80, even more preferably at least eight IMUs 80, of which five IMUs 80 are shown in FIG. 1 for representation. The flexible processing board/micro-processing unit/DAQ 40 is provided with a voltage control 42, a microprocessor 44, and a wireless transmission component/Bluetooth® chip 46. The flexible processing board/micro-processing unit/DAQ 40 and the IMUs 80 are connected to and powered by a flexible power source 30, which in turn receives power between uses from a wireless charging receiver coil 70 when placed in a charging coil's magnetic field.

In operation, as previously noted, the IMUs 80 function as RFID position and/or motion sensors by way of at least one, and possibly multiple, accelerometers, and as gyroscopic sensors, and may further be provided with one or more infrared transceiver/receiver, used alone or with another optical sensor. Again, the information sensed by the IMUs 80 and their infrared transceiver/receivers, if applicable, is packed up by the microprocessor 44 of the flexible processing board/micro-processing unit/DAQ 40 and transmitted wirelessly to a central processor or another device for further processing by the wireless transmission component/Bluetooth® chip 46. Certain parts of the wearable device 10 may be provided with fabric reinforcement 22 for wear purposes, or fabric patches 22 having stretch or movement characteristics differing from the stretch or movement characteristics of the remainder of the wearable device 10, an example of which is shown in FIG. 1 attached by stitching 18 to the remainder of the wearable device 10. This may be done in order to specifically control the location and motion of the IMU 80 attached thereto relative to the patient's knee.

Figure 2:
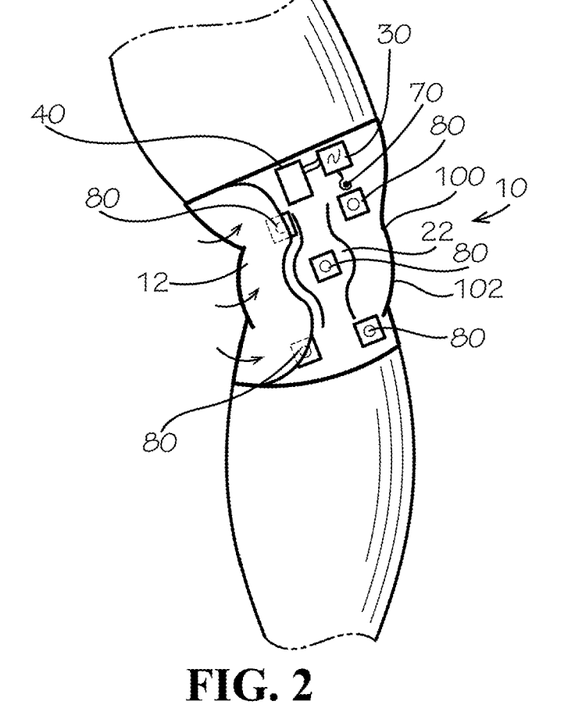
FIG. 2 is a view of an embodiment of a Wearable Device for Measuring Body Kinetics in use on a patient's knee, as described herein.
Figure 3:
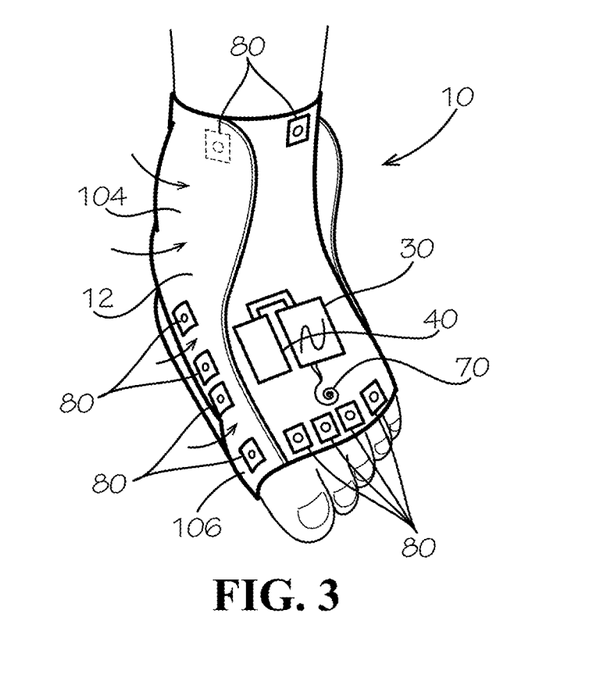
FIG. 3 is a view of an embodiment of a Wearable Device for Measuring Body Kinetics in use on a patient's ankle, as described herein.

Turning now to FIGS. 2 and 3, isometric views of two embodiments of a wearable device 10 are shown. The embodiment of the wearable device 10 shown in FIG. 2 is arranged to provide position, motion, and/or articulation data concerning a patient's knee 100, whereas the embodiment of the wearable device 10 shown in FIG. 3 is arranged to provide position, motion, and/or articulation data concerning a patient's ankle 104. The wearable device 10 is again constructed of fabric, and encircles the patient's knee 100 as shown in FIG. 2, or the patient's foot 106 and ankle 104 as shown in FIG. 3, where it is held by the hook and loop closure 12. The flexible processing board/micro-processing unit/DAQ 40 of the wearable device 10 is again connected to the IMUs 80, and is provided with a voltage control 42, a microprocessor 44, and a wireless transmission component/Bluetooth® chip 46. The flexible processing board/micro-processing unit/DAQ 40 and the IMUs 80 are again connected to the flexible power source 30. The embodiment of the wearable device 10 arranged to provide data concerning a patient's knee 100, for example, may further be provided with a fabric patch 22 having stretch or movement characteristics differing from the stretch or movement characteristics of the remainder of the wearable device 10. In the case of the wearable device 10 shown in FIG. 2, as a non-limiting example, the fabric patch 22 is located over the patient's patella 102.

Figure 4:
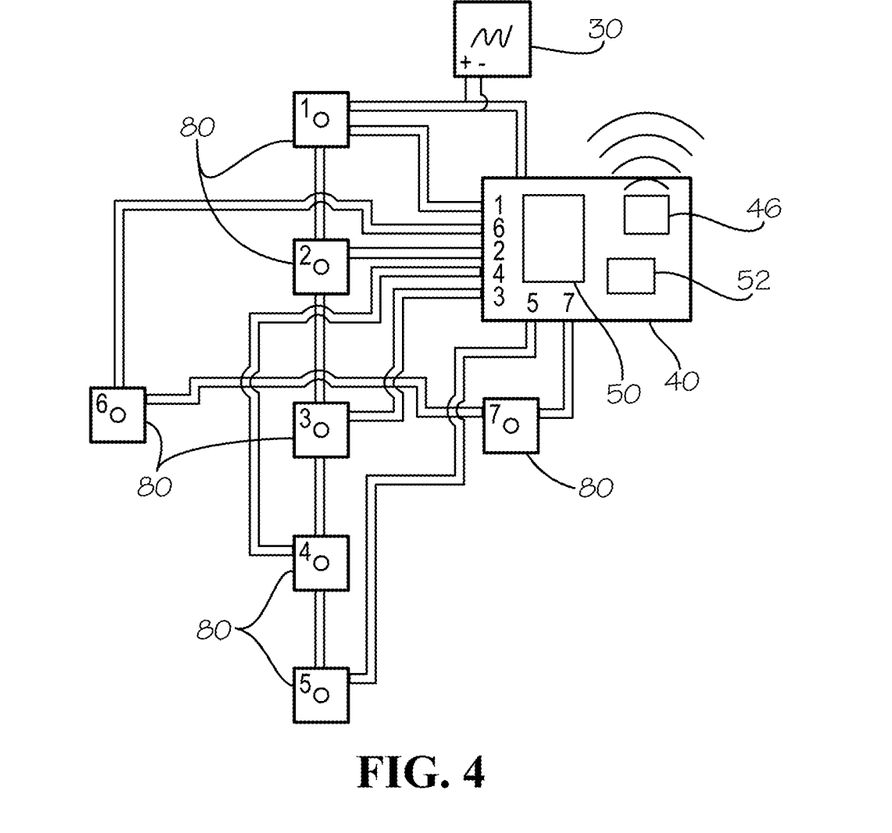
FIG. 4 is a schematic view of an embodiment of a data acquisition component/flexible processing board/micro-processing unit, flexible power source, circuit, and inertial measurement units of a Wearable Device for Measuring Body Kinetics, as described herein.
Figure 5:
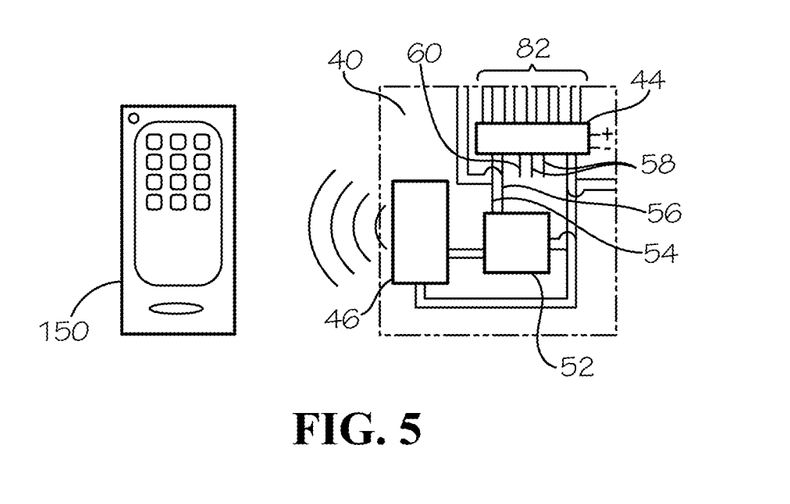
FIG. 5 is a schematic view of an embodiment of a data acquisition component/flexible processing board/micro-processing unit of a Wearable Device for Measuring Body Kinetics and mobile device used therewith, as described herein.

Turning now to FIGS. 4 and 5, schematic views of an embodiment of a circuit having a flexible processing board/micro-processing unit/DAQ 40, a flexible power source 30, and several IMUs 80 is shown. The flexible processing board/micro-processing unit/DAQ 40 has a microprocessor 44 and a wireless transmission component/Bluetooth® chip 46, and may further include a multiplexer 50 and a Master Control Unit (MCU) 52. The MCU 52 is connected to a clock line (SCL) 54 and a data line (SDA) 56, and to the microprocessor 44, from which the MCU 52 receives data, and which may be provided with one or more pull-up resistor connections 58 and a supply bypass capacitor connection 60. In this way, the MCU 52 of the flexible processing board/micro-processing unit/DAQ 40 may be connected to the IMUs 80 by way of the multiplexer 50 and multiplexed IMU connections 82 for robust communication with the IMUs 80. The wireless transmission component/Bluetooth® chip 46 again transmits the data that has been packed up by the microprocessor 44 to a mobile device 150.

While a multiplexed circuit arrangement is shown in FIGS. 4 and 5, this is a non-limiting exemplary embodiment. The Wearable Device for Measuring Body Kinetics may also be embodied with a circuit having the IMUs 80, the infrared transceiver/receivers and/or optical sensors, if applicable, the flexible power source 30, the DAQ/flexible processing board/micro-processing unit 40, and/or the wireless transmission component 46 connected in such a way that the DAQ/flexible processing board/micro-processing unit 40 manages communication in I2C. This may be made possible by the fact that the DAQ/flexible processing board/micro-processing unit 40 may simply collect data from the IMUs 80, the infrared transceiver/receivers, and/or the optical sensors, if applicable, and transmit packed data to the wireless transmission component 46, rather than engage in the two-way exchange of data with any of the aforementioned components. In such an arrangement, a three pin connection minimum is preferable, with a five or six pin connection being even more preferable.

Figure 6:
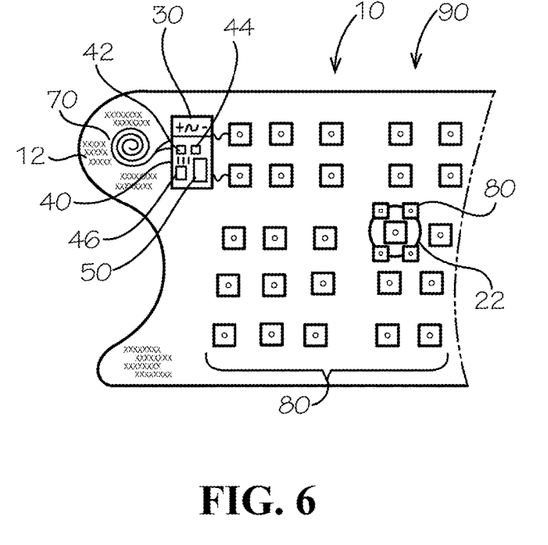
FIG. 6 is a partial plan view of an embodiment of a Wearable Device for Measuring Body Kinetics, as described herein.
Figure 7:
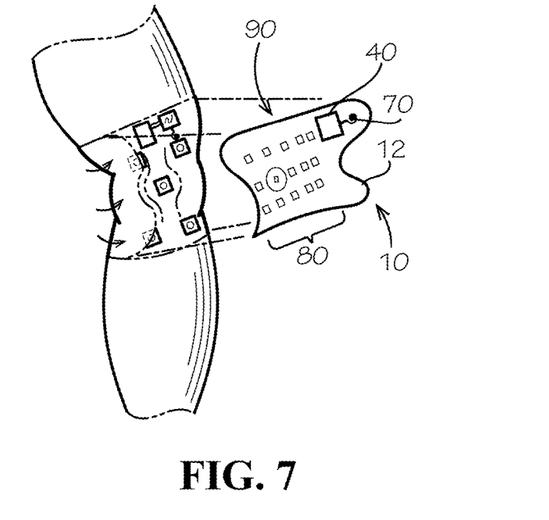
FIG. 7 is a view of an embodiment of a Wearable Device for Measuring Body Kinetics being placed around a patient's knee, as described herein.

Turning now to FIGS. 6 and 7, a partial plan view and an isometric view, respectively of an embodiment of a wearable device 10 is shown. The wearable device 10 is again constructed of fabric, and is provided with a hook and loop closure 12. A flexible processing board/micro-processing unit/DAQ 40 is again connected to at least one IMU 80, preferably at least three IMUs 80, even more preferably at least eight IMUs 80, of which 29 IMUs 80 are shown in FIG. 6 for representation. The IMUs 80 shown in FIGS. 6 and 7 are arranged in a sensor layout 90, which is shown in FIG. 6 in the flat calibration position, and are shown in FIG. 7 in the process of being engaged with a patient's knee joint. The flexible processing board/micro-processing unit/DAQ 40 is again provided with a voltage control 42, a microprocessor 44, and a wireless transmission component/Bluetooth® chip 46, and may or may not be provided with a multiplexer 50. The flexible processing board/micro-processing unit/DAQ 40 and the IMUs 80 are again connected to and powered by a flexible power source 30, which again receives power between uses from a wireless charging receiver coil 70 when placed in a charging coil's magnetic field.

Figure 8:
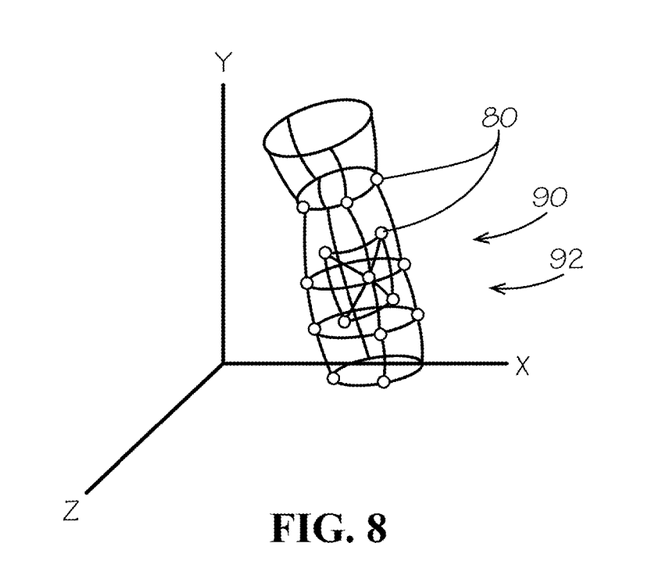
FIG. 8 is a three dimensional scatter plot of the relative location of several inertial measurement units of a Wearable Device for Measuring Body Kinetics in use, as described herein.

FIG. 8, then, shows the sensor layout 90 as represented, in at least one embodiment on a computer screen, in a three axis 3D scatter plot 92. The IMUs 80 are represented by nodes connected by lines to form a wireframe visual of the wearable device 10. The coordinates of each node may again change based on the position and/or motion data from the IMUs 80. Curvature in the lines may again be calculated both during calibration to reflect the radial properties of the body, and may be refined during testing when there is movement. The IMUs 80 and their onscreen nodes may again be located at critical points for gathering data on each joint, represented here in non-limiting example as the knee joint. Note that there may be a concentration of IMUs 80 at the aforementioned fabric patch 22

Figure 9:
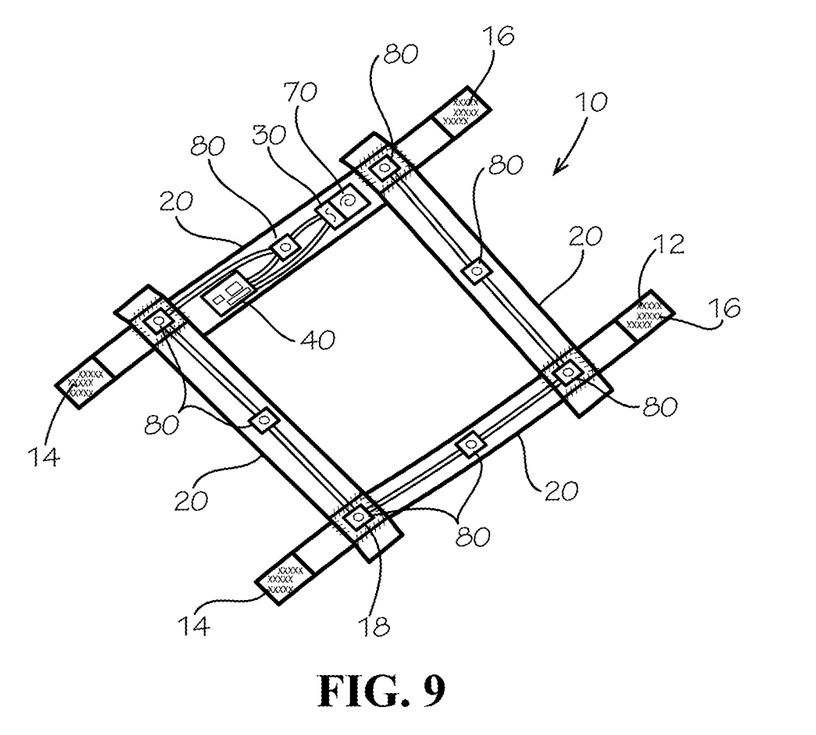
FIG. 9 is an isometric view of a strap or tape embodiment of a Wearable Device for Measuring Body Kinetics, as described herein.

Turning now to FIG. 9, a strap embodiment of the wearable device 10 is shown. In the strap embodiment of the wearable device 10, two or more straps 20 are connected by stitching 18 to provide a strap construct. The circuit having the IMUs 80, the infrared transceiver/receivers and/or optical sensors, if applicable, the flexible power source 30, the DAQ/flexible processing board/micro-processing unit 40, the wireless transmission component 46 (not shown) and/or the wireless charging receiver coil 70 is then attached to the strap construct. In this way, the strap construct secures the IMUs 80 in their proper locations needed to gather data regarding a joint, while leaving other areas open for freedom of movement, ventilation, and/or avoidance of contact with a wound site, as non-limiting examples. The strap embodiment of the wearable device 10 again encircles the joint and is held in place by a hook and loop closure 12 wherein the hooks 14 are located on the outer surface at one end of the wearable device 10 and the loops 16 are on located on the inner surface at the other end of the wearable device 10.

Although not shown in FIG. 9, the straps of the strap embodiment of the wearable device 10 may be adjustable, so that the circumferential straps extending around, for non-limiting example, the leg may be extended or contracted, according to the size of the leg of the patient. The longitudinal straps extending, for non-limiting example, between above the knee and below the knee may also be extended or contracted, according to the size of the knee of the patient. In this way, the strap embodiment of the wearable device 10 may be adjusted to fit different knee sizes, as well as being easily adjusted to move up and down and/or side to side about the knee, while still lying flat and avoiding contact with any wound site. This may avoid any compression against an incision that would cause discomfort or cause the patient to avoid using the joint. This may also provide beneficial airflow to the wound and avoid accumulation of warmth and moisture that would facilitate growth of bacteria.

Figure 10:
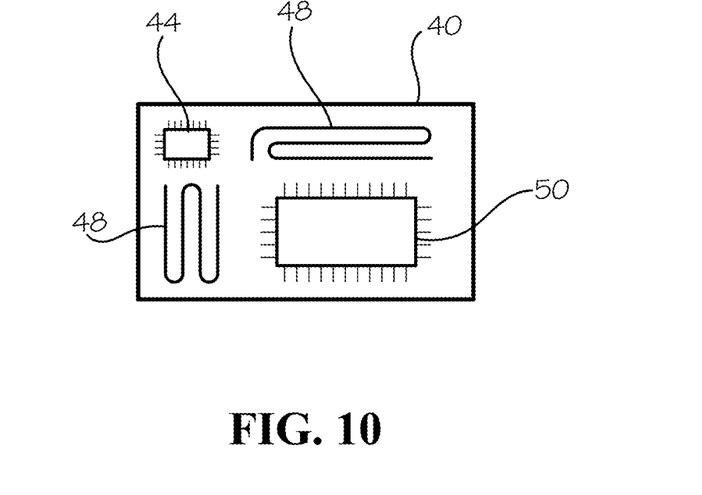
FIG. 10 is a partial schematic view of an embodiment of a data acquisition component/flexible processing board/ micro-processing unit of a Wearable Device for Measuring Body Kinetics, as described herein.

Turning now to FIG. 10, a partial schematic of a flexible processing board/micro-processing unit/DAQ 40 is shown for the purpose of Illustrating possible arrangements of antennae 48. A few of the components of the flexible processing board/micro-processing unit/DAQ 40, such as the microprocessor 44 and the multiplexer 50 are shown for illustrative purposes. It is noted that the antennae 48 which may be used by the wireless transmission component/Bluetooth® chip may be arranged in perpendicular locations, so that one antenna 48 may be arranged vertically and the other antenna 48 may be arranged horizontally.

While the Wearable Device for Measuring Body Kinetics has been described with respect to at least one embodiment, the Wearable Device for Measuring Body Kinetics can be further modified within the spirit and scope of this disclosure, as demonstrated previously. This application is therefore intended to cover any variations, uses, or adaptations of the Wearable Device for Measuring Body Kinetics using its general principles. Further, this application is intended to cover such departures from the present disclosure as come within known or customary practice in the art to which the disclosure pertains and which fall within the limits of the appended claims.

REFERENCE NUMBER LISTING

10 Wearable Device
12 Hook and Loop Closure
14 Hooks
16 Loops
18 Stitching
20 Straps
22 Fabric patch
30 Flexible Power Source
40 Flexible Processing Board/Micro-Processing Unit/Data Acquisition Component (DAQ)
42 Voltage Control
44 Microprocessor
46 Wireless Transmission Component/Bluetooth® Chip
48 Antenna
50 Multiplexer
52 Master Control Unit (MCU)
54 Clock line (SCL)
56 Data line (SDA)
58 Pull-up resistor connections
60 Supply bypass capacitor connection
70 Wireless Charging Receiver Coil
80 Inertial Measurement Unit (IMU)
82 IMU connections
90 Sensor Layout
92 3D Scatter Plot
100 Knee
102 Patella
104 Ankle
106 Foot
120 Qualitative Targets
122 Ligaments
124 Ankle Tendons
126 ACL
128 MCL
130 LCL
132 Meniscus
134 PCL
150 Mobile device

What is claimed is:

1. A System for Measuring Body Kinetics, comprising:
a wearable device configured to be wrapped around a joint;
a microprocessor attached to the wearable device;
at least one Inertial Measurement Unit (IMU) connected to the microprocessor and arranged on the wearable device, the at least one IMU being arranged and configured to provide kinetic data concerning the joint to the microprocessor;
at least one infrared transceiver/receiver connected to the microprocessor and arranged on the wearable device, the at least one infrared transceiver/receiver being arranged and configured to provide qualitative movement data by way of sensing wavelengths of light emitted or reflected in the near infrared spectrum;

a wireless transmission component connected to the microprocessor, wherein the microprocessor is configured to receive kinetic data from the at least one IMU and qualitative movement data from the at least one infrared transceiver/receiver, and to transmit the kinetic data and the qualitative movement data by way of the wireless transmission component to a central processor or other device; and an algorithm residing within at least one of the microprocessor and the central processor or other device, the algorithm being configured to determine the position of each IMU from the kinetic data, and to pair or correlate the qualitative movement data with the kinetic data.

2. The System of claim 1, wherein:
the at least one IMU and the at least one infrared transceiver/receiver being connected to the microprocessor by way of at least one of an electronic circuit and a local wireless network.

3. The System of claim 1, wherein at least one of:
the at least one infrared transceiver/receiver is integrated with the at least one IMU; and
the wavelengths of light sensed by the at least one infrared transceiver/receiver being actively varied.

4. The System of claim 1, wherein:
the wearable device being constructed of at least one of fabric, strap, and adhesive tape.

5. The System of claim 1, wherein:
the at least one IMU further comprising at least one of:
 at least one accelerometer providing at least one of linear position, linear velocity, linear acceleration, and rate of change of linear acceleration of the at least one IMU; and
 at least one gyroscopic sensor providing at least one of angular position, angular velocity, angular acceleration, and rate of change of angular acceleration of the at least one IMU.

6. The System of claim 1, wherein:
the at least one IMU being further capable of radio frequency identification.

7. The System of claim 1, wherein:
the microprocessor being further configured to pack up the kinetic data and the qualitative movement data before transmitting it by way of the wireless transmission component.

8. The System of claim 1, wherein:
the algorithm being further configured to at least one of:
 generate a 3D model of the joint from the kinetic data;
 present the location of each IMU as a node in a 3D scatter plot;
 determine at least one of a force and an impact within the joint;
 determine movement of at least one of muscles, tendons, and ligament fibers; and
 determine at least one of blood flow, oxygenation, and metabolic activity.

9. The System of claim 1, wherein:
the microprocessor and the at least one IMU being connected by way of a multiplexer.

10. The System of claim 1, further comprising:
a fabric patch having stretch or movement characteristics differing from the stretch or movement characteristics of the wearable device, the fabric patch being attached to the wearable device, and at least one IMU being arranged on the fabric patch.

11. A Wearable Device for Measuring Body Kinetics, comprising:
a wearable device configured to be wrapped around a joint;
a microprocessor attached to the wearable device;
at least one Inertial Measurement Unit (IMU) connected to the microprocessor and arranged on the wearable device, the at least one IMU being arranged and configured to provide kinetic data concerning the joint to the microprocessor;
at least one infrared transceiver/receiver connected to the microprocessor and arranged on the wearable device, the at least one infrared transceiver/receiver being arranged and configured to provide qualitative movement data by way of sensing wavelengths of light emitted or reflected in the near infrared spectrum;
a wireless transmission component connected to the microprocessor, wherein the microprocessor is configured to receive kinetic data from the at least one IMU and qualitative movement data from the at least one infrared transceiver/receiver, and to transmit the kinetic data and the qualitative movement data by way of the wireless transmission component to a central processor or other device; and
an algorithm residing within the microprocessor, the algorithm being configured to pair or correlate the qualitative movement data with the kinetic data.

12. The Wearable Device of claim 11, wherein:
the at least one IMU and the at least one infrared transceiver/receiver being connected to the microprocessor by way of at least one of an electronic circuit and a local wireless network.

13. The Wearable Device of claim 11, wherein at least one of:
the at least one infrared transceiver/receiver is integrated with the at least one IMU; and
the wavelengths of light sensed by the at least one infrared transceiver/receiver being actively varied.

14. The Wearable Device of claim 11, wherein:
the wearable device being constructed of at least one of fabric, strap, and adhesive tape.

15. The Wearable Device of claim 11, wherein:
the at least one IMU further comprising at least one of:
 at least one accelerometer providing at least one of linear position, linear velocity, linear acceleration, and rate of change of linear acceleration of the at least one IMU; and
 at least one gyroscopic sensor providing at least one of angular position, angular velocity, angular acceleration, and rate of change of angular acceleration of the at least one IMU.

16. The Wearable Device of claim 11, wherein:
the at least one IMU being further capable of radio frequency identification.

17. The Wearable Device of claim 11, further comprising:
the microprocessor being further configured to pack up the kinetic data and the qualitative movement data before transmitting it by way of the wireless transmission component.

18. The Wearable Device of claim 11, wherein:
the microprocessor and the at least one IMU being connected by way of a multiplexer.

19. The Wearable Device of claim 11, further comprising:
a fabric patch having stretch or movement characteristics differing from the stretch or movement characteristics of the wearable device, the fabric patch being attached to the wearable device, and at least one IMU being arranged on the fabric patch.

20. A Method for Measuring Body Kinetics, comprising the steps of:
- configuring a wearable device to be wrapped around a joint;
- attaching a microprocessor to the wearable device;
- arranging at least one Inertial Measurement Unit (IMUS on the wearable device and connecting the at least one IMU to the microprocessor;
- configuring the at least one IMU to provide kinetic data concerning the joint to the microprocessor;
- arranging at least one infrared transceiver/receiver on the wearable device and connecting the at least one infrared transceiver/receiver to the microprocessor;
- configuring the at least one infrared transceiver/receiver to provide to the microprocessor qualitative movement data sensed by way of wavelengths of light emitted or reflected in the near infrared spectrum;
- configuring the microprocessor to receive the kinetic data from the at least one IMU and to receive the qualitative movement data from the at least one infrared transceiver/receiver;
- connecting a wireless transmission component to the microprocessor;
- transmitting the kinetic data and the qualitative movement data by way of the wireless transmission component to a central processor or other device; and
- configuring an algorithm residing within at least one of the microprocessor and the central processor or other device to determine the position of each IMU from the kinetic data and to pair or correlate the qualitative movement data with the kinetic data.

21. The Method of claim 20, further comprising the steps of:
- configuring the algorithm to at least one of:
- generate a 3D model of the joint from the kinetic data;
- present the location of each IMU as a node in a 3D scatter plot;
- determine at least one of a force and an impact within the joint;
- determine movement of at least one of muscles, tendons, and ligament fibers; and
- determine at least one of blood flow, oxygenation, and metabolic activity.

\* \* \* \* \*